US011512821B2

(12) United States Patent
Pollastri et al.

(10) Patent No.: US 11,512,821 B2
(45) Date of Patent: Nov. 29, 2022

(54) SYSTEMS AND METHOD FOR EVALUATING ULTRAVIOLET-PROTECTION PRODUCTS

(71) Applicant: ABICH INC., Montreal (CA)

(72) Inventors: Michela Pollastri, Montreal (CA); Debora Pischedda, Montreal (CA); Mariana Riad, Brossard (CA)

(73) Assignee: ABICH INC., Montreal (CA)

( * ) Notice: Subject to any disclaimer, the term of this patent is extended or adjusted under 35 U.S.C. 154(b) by 0 days.

(21) Appl. No.: 17/075,976

(22) Filed: Oct. 21, 2020

(65) Prior Publication Data

US 2021/0116082 A1 Apr. 22, 2021

Related U.S. Application Data

(60) Provisional application No. 62/923,863, filed on Oct. 21, 2019.

(51) Int. Cl.
*A61K 49/00* (2006.01)
*F21S 8/00* (2006.01)
*F21V 21/00* (2006.01)

(52) U.S. Cl.
CPC .......... *F21S 8/006* (2013.01); *A61K 49/0006* (2013.01); *F21V 21/00* (2013.01)

(58) Field of Classification Search
CPC ............................. A61K 49/0006; F21S 8/006
USPC ........................................................ 362/1–2
See application file for complete search history.

(56) References Cited

U.S. PATENT DOCUMENTS

| 7,567,080 B2 | 7/2009 | Ferrero et al. |
| 10,732,100 B2 | 8/2020 | Haddad et al. |
| 2009/0168436 A1* | 7/2009 | Ford ........................ F21V 3/04 362/355 |
| 2018/0321139 A1 | 11/2018 | Helfmann et al. |

FOREIGN PATENT DOCUMENTS

| GB | 2325048 A | 11/1998 |
| WO | 2008/038135 A3 | 4/2008 |

\* cited by examiner

*Primary Examiner* — Sean P Gramling
(74) *Attorney, Agent, or Firm* — Schneider IP Law LLC; Laura Schneider

(57) ABSTRACT

There is provided a system for evaluating an ultraviolet-protection product to be applied to skin, including a light source generating an output beam and a spacer mountable to the light source for maintaining a fixed distance between the light source and the skin. The spacer includes a mounting bracket engageable with the light source and a frame mechanically connected to the mounting bracket and extending longitudinally outwardly from the mounting bracket, the frame comprising an outer periphery, an inner periphery and a skin-contacting portion, the inner periphery defining a hollow region therein, such that when the skin-contacting portion is engaged with the skin, the beam passes through the hollow region and interacts with the skin at an illumination plane to define an illuminated area confined within the hollow region, the ultraviolet-protection product remaining substantially unaffected in the illuminated area upon relative movement of the skin with respect to the frame.

17 Claims, 10 Drawing Sheets

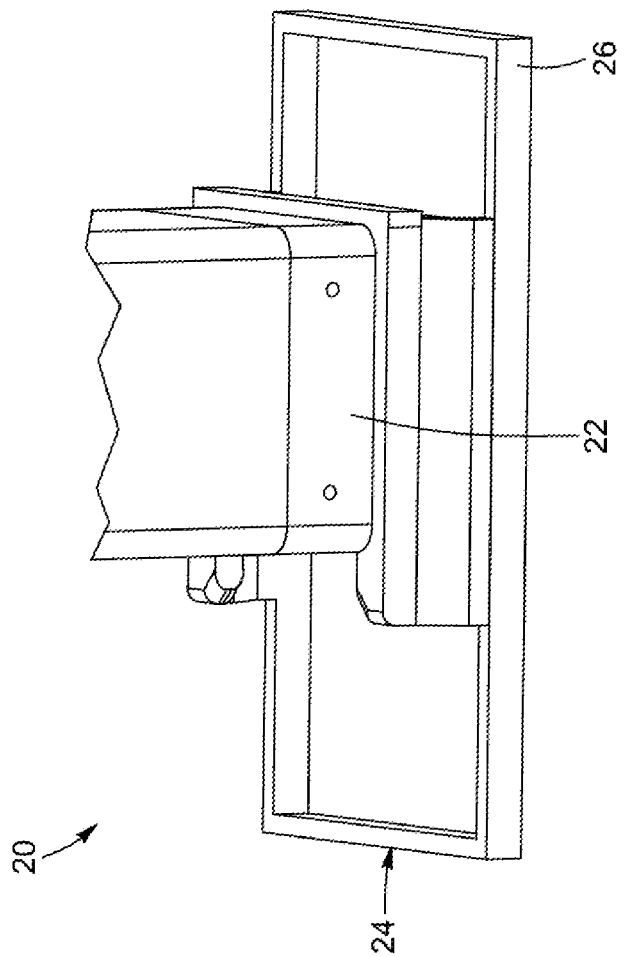

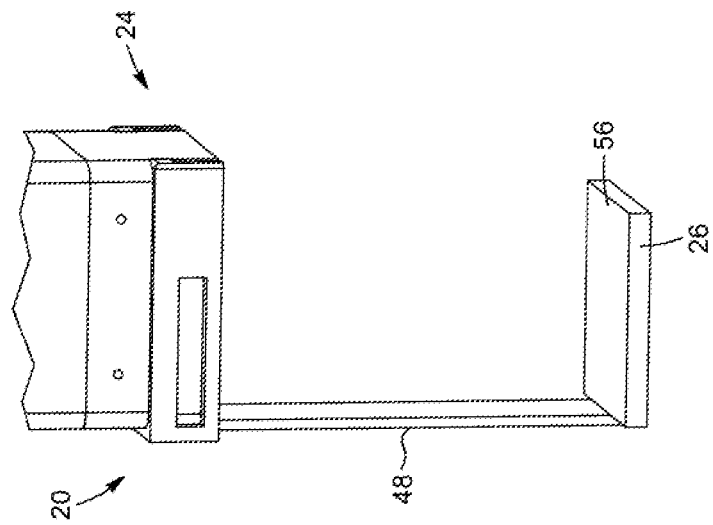
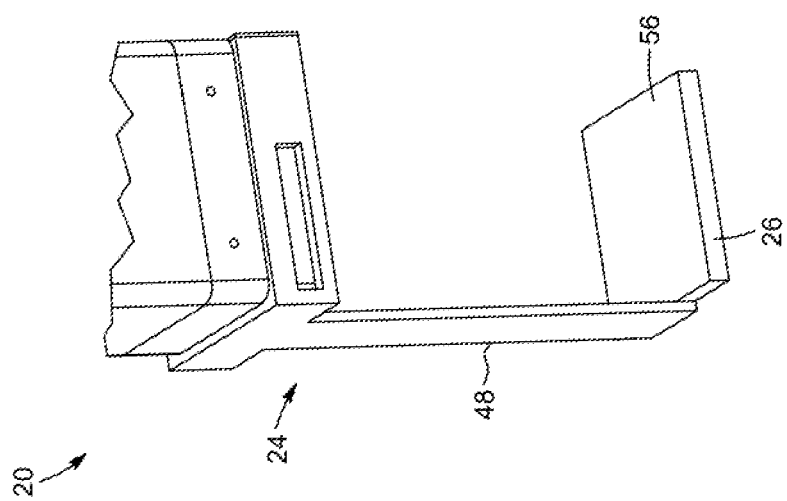

SYSTEMS AND METHOD FOR EVALUATING ULTRAVIOLET-PROTECTION PRODUCTS

RELATED APPLICATION

This patent application claims the benefit of the filing date of U.S. Patent Application Ser. No. 62/923,863, filed Oct. 21, 2019, the contents of which are incorporated herein by reference.

TECHNICAL FIELD

The technical field generally relates to devices, related systems, as well as methods for evaluating ultraviolet-protection products, and more particularly relates to systems and methods for evaluating, either in vivo or in vitro, an ultraviolet-protection product, such as solar protection products, coating a skin or a sample or to be applied to the same.

BACKGROUND

Solar protection products are well known products that absorb or reflect some of the potentially damageable radiation emitted by the Sun, such as, for example, ultraviolet (UV) radiation. When applied to the skin, a solar protection product generally helps protecting against or at least reducing the probability of sunburn.

A common way of classifying or evaluating the solar protection products is the Sun protection factor (SPF), which provides an indication of the efficiency of the solar protection products. The SPF is generally representative of measurements of the fraction of sunburn producing UV radiation that reaches the skin when a solar protection product is provided thereon. Such measurements can either be carried out in vivo or in vitro.

Systems, devices, methods and techniques are available for evaluating solar protection products and determining the SPF of these products. However, the results provided by known techniques generally suffer from poor reliability, reproducibility and large variance.

There is thus a need for a system, device, as well as methods that address or alleviate at least some of the challenges presented above.

SUMMARY

In accordance with one aspect, there is provided a system for evaluating an ultraviolet-protection product to be applied to skin, comprising a light source generating an output beam having a natural light spectral profile; and a spacer mountable to the light source for maintaining a fixed distance between the light source and the skin, the spacer comprising: a mounting bracket engageable with the light source; and a frame mechanically connected to the mounting bracket and extending longitudinally outwardly from the mounting bracket, the frame comprising an outer periphery, an inner periphery and a skin-contacting portion, the inner periphery defining a hollow region therein, such that when the skin-contacting portion is engaged with the skin, the output beam passes through the hollow region and interacts with the skin at an illumination plane to define an illuminated area confined within the hollow region, the ultraviolet-protection product remaining substantially unaffected in the illuminated area upon relative movement of the skin with respect to the frame.

In some embodiments, the light source is a sun simulator.

In some embodiments, the natural light spectral profile ranges from about 250 nm to about 2500 nm.

In some embodiments, the natural light spectral profile comprises a UVA band and a UVB band.

In some embodiments, the light source comprises a plurality of light emitters, each being configured to generate a respective sub-beam.

In some embodiments, the mounting bracket is clipped on the light source.

In some embodiments, the mounting bracket is slidably engageable with the light source.

In some embodiments, the mounting bracket has a pair of rails mechanically engageable with a corresponding pair of guides provided on the light source.

In some embodiments, the light source has an illumination output portion, the spacer being mountable to the illumination output portion of the light source.

In some embodiments, the frame comprises four sidewalls.

In some embodiments, the frame has a rectangular cross-section extending substantially parallel to the illumination plane.

In some embodiments, the spacer is made from a UV light resistant material.

In some embodiments, the spacer is made from a low thermal conductivity material.

In some embodiments, the spacer is made from a high-temperature resistant material.

In some embodiments, the spacer is made from a biocompatible material.

In some embodiments, the biocompatible material is selected from the group consisting of polyurethane, polyamide, titanium, stainless steel, ultra high molecular weight polyethylene, medical grade silicone, poly(methyl methacrylate), acrylonitrile butadiene styrene, polyetherimide, polyether ether ketone, polyetherketoneketone, acrylonitrile styrene acrylate and polycarbonate.

In some embodiments, the system further comprises an elongated member having a top portion and a bottom portion, the top portion being connected to the mounting bracket and the bottom portion being connected to the frame, the elongated member longitudinally extending from the top portion towards the bottom portion in a substantially vertical direction, substantially perpendicular to the illumination plane.

In some embodiments, the spacer is compliant with at least one of FDA 2011, ISO 24444, ISO 24442 and Colipa method.

In accordance with another aspect, there is provided a spacer mountable to a light source associated with a system for evaluating an ultraviolet-protection product to be applied to skin, the light source being configured to generate an output beam having a natural light spectral profile, the spacer comprising a mounting bracket engageable with the light source; and a frame mechanically connected to the mounting bracket and extending longitudinally outwardly from the mounting bracket, the frame comprising an outer periphery, an inner periphery and a skin-contacting portion, the inner periphery defining a hollow region therein, such that when the skin-contacting portion is engaged with the skin, the output beam passes through the hollow region and interacts with the skin at an illumination plane to define an illuminated area confined within the hollow region, the ultraviolet-protection product remaining substantially unaffected in the illuminated area upon relative movement of the skin with respect to the frame.

In accordance with another aspect, there is provided a system for evaluating an ultraviolet-protection product coating a sample, comprising a light source generating an output beam having a natural light spectral profile, the output beam interacting with the sample at an illumination plane to define an illuminated area; and a spacer mountable to the light source for maintaining a fixed distance between the light source and the sample, the spacer comprising a mounting bracket engageable with the light source; and a frame mechanically connected to the mounting bracket, the frame comprising a sample stage for receiving the sample thereon; and an elongated member having a top portion and a bottom portion, the top portion being connected to the mounting bracket and the bottom portion being connected with the frame, the elongated member longitudinally extending from the top portion towards the bottom portion in a vertical direction substantially perpendicular to the illumination plane.

In some embodiments, the light source is a sun simulator.

In some embodiments, the natural light spectral profile ranges from about 250 nm to about 2500 nm.

In some embodiments, the natural light spectral profile comprises a UVA band and a UVB band.

In some embodiments, the light source comprises a plurality of light emitters, each being configured to generate a respective sub-beam.

In some embodiments, the mounting bracket is clipped on the light source.

In some embodiments, the mounting bracket is slidably mountable to the light source.

In some embodiments, the mounting bracket has a pair of rails mechanically engageable with a corresponding pair of guides provided on the light source.

In some embodiments, the light source has an illumination output portion, the spacer being mountable to the illumination output portion of the light source.

In some embodiments, the frame comprises four sidewalls.

In some embodiments, the frame has a rectangular cross-section extending substantially parallel to the illumination plane.

In some embodiments, the spacer is made from a UV light resistant material.

In some embodiments, the spacer is made from a low thermal conductivity material.

In some embodiments, the spacer is made from a high-temperature resistant material.

In some embodiments, the spacer is made from a biocompatible material.

In some embodiments, the biocompatible material is selected from polyurethane, polyamide, titanium, stainless steel, ultra high molecular weight polyethylene, medical grade silicone, poly(methyl methacrylate), acrylonitrile butadiene styrene, polyetherimide, polyether ether ketone, polyetherketoneketone, acrylonitrile styrene acrylate and polycarbonate.

In some embodiments, the spacer is compliant with at least one of FDA 2011, ISO 24444, ISO 24442 and Colipa method.

In accordance with another aspect, there is provided a spacer mountable to a light source associated with a system for evaluating an ultraviolet-protection product coating a sample, the light source being configured to generate an output beam having a natural light spectral profile, the spacer comprising a mounting bracket engageable with the light source; and a frame mechanically connected to the mounting bracket, the frame comprising a sample stage for receiving the sample thereon; and an elongated member having a top portion and a bottom portion, the top portion being connected to the mounting bracket and the bottom portion being connected with the frame, the elongated member longitudinally extending from the top portion towards the bottom portion in a vertical direction substantially perpendicular to the illumination plane.

In accordance with another aspect, there is provided a method for evaluating, using a light source, an ultraviolet-protection product to be applied to skin, the method comprising contacting the skin with a spacer mounted to the light source to maintain a fixed distance between the light source and the skin, the spacer comprising a mounting bracket engageable with the light source and a frame mechanically connected to the mounting bracket and extending longitudinally outwardly from the mounting bracket, the frame comprising an outer periphery, an inner periphery and a skin-contacting portion, the inner periphery defining a hollow region therein; and generating an output beam having a natural light spectral profile with the light source towards the skin, the output beam passing through the hollow region and interacting with the skin at an illumination plane to define an illuminated area confined within the hollow region, the ultraviolet-protection product remaining substantially unaffected in the illuminated area upon relative movement of the skin with respect to the frame.

In accordance with another aspect, there is provided a method for evaluating, using a light source, an ultraviolet-protection product coating a sample, the method comprising providing a spacer mounted to the light source to maintain a fixed distance between the light source and the sample, the spacer comprising a mounting bracket engageable with the light source, a frame mechanically connected to the mounting bracket, the frame comprising a sample stage for receiving the sample thereon and an elongated member having a top portion and a bottom portion, the top portion being connected to the mounting bracket and the bottom portion being connected with the frame, the elongated member longitudinally extending from the top portion towards the bottom portion in a vertical direction substantially perpendicular to the illumination plane; mounting the sample on the sample stage; and generating an output beam having a natural light spectral profile with the light source towards the sample.

Other features and advantages of the present description will become more apparent upon reading of the following non-restrictive description of specific embodiments thereof, given by way of example only with reference to the accompanying drawings.

BRIEF DESCRIPTION OF THE DRAWINGS

FIGS. 1A-F illustrate a system for evaluating ultraviolet-protection products, in accordance with one embodiment, and an embodiment of an apparatus for maintaining a fixed distance between a light source and a sample under investigation, such as skin.

FIGS. 4A-B illustrate a system for evaluating ultraviolet-protection products, in accordance with one embodiment.

DETAILED DESCRIPTION

Figure 1B:
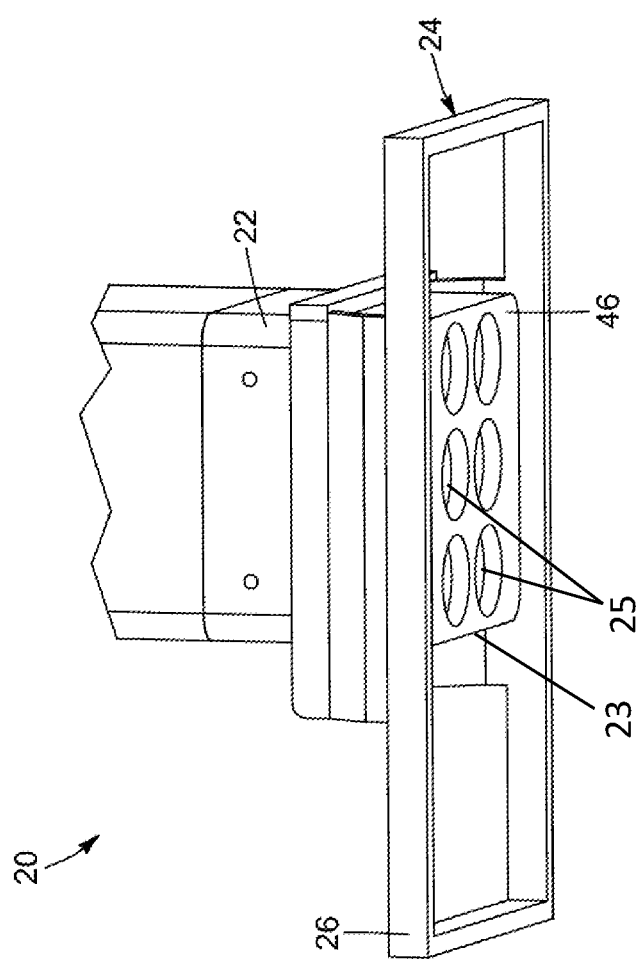
Figure 1D:
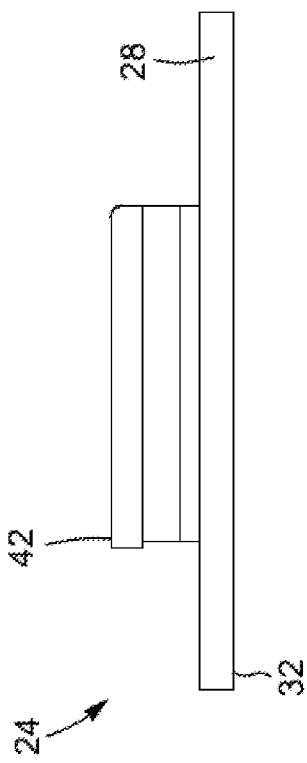
Figure 1C:
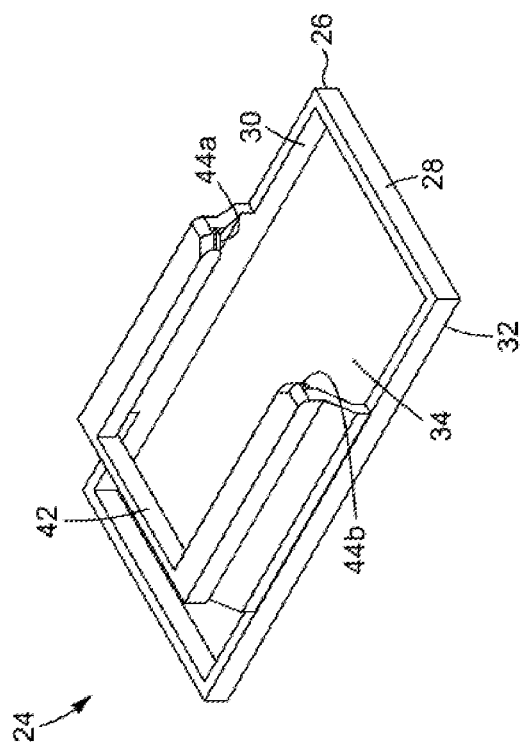
Figure 1F:
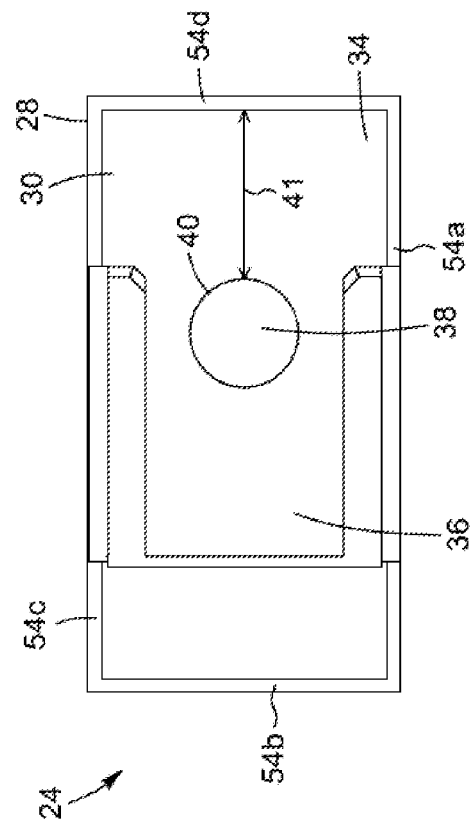
Figure 1E:
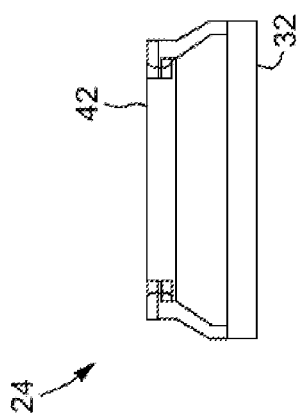

In the present description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The terms "a", "an" and "one" are defined herein to mean "at least one", that is, these terms do not exclude a plural number of elements, unless stated otherwise. It should also be noted that terms such as "substantially", "generally" and "about", that modify a value, condition or characteristic of a feature of an exemplary embodiment, should be understood to mean that the value, condition or characteristic is defined within tolerances that are acceptable for the proper operation of this exemplary embodiment for its intended application.

In the present description, the terms "connected", "coupled", and variants and derivatives thereof, refer to any connection or coupling, either direct or indirect, between two or more elements. The connection or coupling between the elements may be mechanical, physical, optical, operational, electrical, wireless, or a combination thereof.

It will be appreciated that positional descriptors indicating the position or orientation of one element with respect to another element are used herein for ease and clarity of description and should, unless otherwise indicated, be taken in the context of the figures and should not be considered limiting. It will be understood that spatially relative terms (e.g., "outer" and "inner", and "top" and "bottom") are intended to encompass different positions and orientations in use or operation of the present embodiments, in addition to the positions and orientations exemplified in the figures.

In the present description, the terms "light" and "optical", and any variants and derivatives thereof, are intended to refer to electromagnetic radiation in any appropriate region of the electromagnetic spectrum and are not limited to visible light. For example, in one embodiment, the terms "light" and "optical" may encompass electromagnetic radiation with a wavelength ranging from about 280 nm to about 400 nm. More particularly, although some embodiments of the present techniques can be useful in broad range applications, other embodiments can additionally or alternatively operate in other regions of the electromagnetic spectrum, for example in the millimeter, terahertz, infrared and ultraviolet regions.

In the present description, the expression "natural light" and similar expressions and variants thereof refer to the light emitted by the Sun or a lamp reproducing the natural light (e.g., a sun simulator), and more particularly the spectral profile of the Sun. One skilled in the art will understand that the natural light has similar spectral characteristics as light of the Sun reaching the Earth's surface. As such, the natural light has a natural spectral profile that is defined as being the variation in light intensity as a function of wavelengths. As known to those skilled in the art, the spectral profile of light from the Sun can vary depending on several factors such as the time of the day, the period of the year, the geographic location and several other factors.

The expressions "solar protection product", "ultraviolet-protection product", "sunscreen", synonyms and variants thereof will be used throughout the present description. These expressions encompass a broad variety of protection techniques against the sun, and so can be provided, for example, as a lotion, a spray, a gel, a foam, a powder or the like. These protection techniques can take the form of a product applicable on the skin, the product either absorbing or reflecting some of the sun's electromagnetic radiation. It will be understood that in the context of preventing sunburns, the ultraviolet (UV) components of the sun's electromagnetic radiation can be of particular interest. The ultraviolet-protection products can generally be classified into two broad classes. The first class is "physical ultraviolet-protection product" and relates to products that generally deflect the sun's electromagnetic radiation from the skin. Known examples of such physical solar products include but are not limited to zinc oxide and titanium dioxide. The second class is "chemical ultraviolet-protection product" and relates to products that absorb the UV light. An example of such chemical ultraviolet-protection product are UV organic filters.

Broadly described, there is provided a system for evaluating an ultraviolet-protection product coating a skin or a sample. This system can either be used for in vivo implementations or in vitro implementations. Tests for evaluating ultraviolet-protection products are generally conducted in laboratory, wherein samples are covered or coated with an ultraviolet-protection product and subsequently exposed to a light source resembling the light emitted by the Sun. The samples, which can be skin, are then monitored and characterized in order to evaluate the effectiveness of the ultraviolet-protection products. A broad variety of tests are known and used in the art, some of them will be described in greater detail herein.

Some of the experiments for evaluating ultraviolet-protection products can be carried out in vivo, i.e., on a living subject. In these instances, a portion of the skin of the subject is covered with the ultraviolet-protection product and then exposed to light to evaluate the effectiveness of the ultraviolet-protection product. Other experiments can be carried in vitro, for examples and without being limitative, plastic support like PMMA (poly-methyl-methacrylate) plates, HelioScreen plates or any suitable plastic substrate.

Different methods, protocols, standard methods and experimental procedures exist for assessing or determining the properties of the ultraviolet-protection products, for example the SPF. Nonlimitative examples of these methods are FDA 2011, ISO 24444, ISO 24442 and Colipa method. These techniques generally involve inducing an erythema spot on participants' skin or sample on which the ultraviolet-protection product has been provided. The skin type of participants, as well as their number, can vary depending on the technique being used. Generally, the light sensitivity of the skin or sample is characterized prior to its exposition to the light conditions under which the tests will be performed. Such a step allows determining the minimal erythemal dose of the participant or sample. A predetermined amount of the ultraviolet-protection product can then be dispensed on the participants' skin or sample to coat the skin or the sample with the ultraviolet-protection product. In the case of in vivo experiments, the ultraviolet-protection product can be dispensed on the back of the participant. After a predetermined amount of time, the skin or the sample is progressively exposed to the light conditions and the evolution of the skin or the sample is visually assessed. The results of these tests generally establish how long the ultraviolet-protection products can extend the exposure to the light conditions before the apparition on an erythema, in comparison with a skin or sample without the ultraviolet-protection products.

One challenge with the conventional techniques and systems is associated with the fact that, especially in the case of in vivo sample, the participant having his/her skin coated with the ultraviolet-protection product may move, which will not only change the distance between the participant's skin and the light source (therefore affecting the dose and exposure), but may also push or move the ultraviolet-protection product, which can result in a non-uniform distribution of ultraviolet-protection product on the skin (i.e., the thickness of the product can vary depending on its location on the participant's body). This non-uniformity in the distribution of the ultraviolet-protection product affect the reliability, reproducibility and the variance of the experiments, thus rendering the evaluation of ultraviolet-protection products challenging.

Figure 2A:
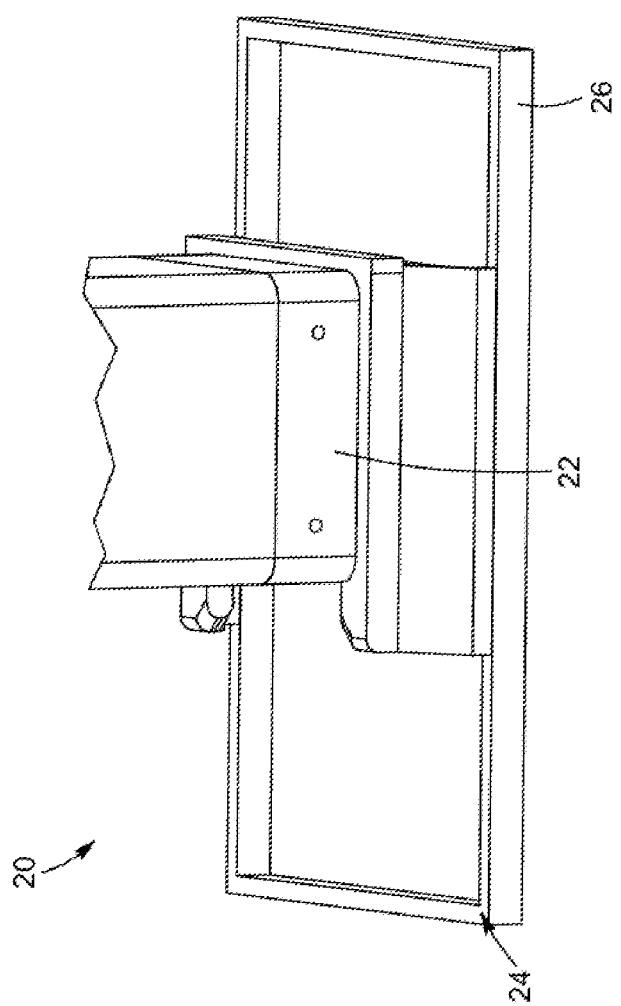
FIGS. 2A-B illustrate a system for evaluating ultraviolet-protection products, in accordance with one embodiment.

System for Evaluating an Ultraviolet-Protection Product Coating a Skin or Sample Now turning to the FIGS. 1 to 3, different embodiments of a system 20 for evaluating an ultraviolet-protection product coating a skin or a sample, are shown.

The system 20 generally includes a light source 22. The light source 22 is configured to generate an output beam towards the skin being covered by the ultraviolet-protection product, or without ultraviolet-protection production, depending on the phase of the test. The output beam, which can sometimes be referred to as the illumination beam, has a natural light spectral profile. As it has been previously mentioned, the natural light spectral profile generally resembles the spectral profile of the sun.

The light source 22 can be embodied by a broad variety of devices, as long as they can be configured to emit an output beam having the required characteristics for the targeted applications. In some embodiments, the light-source comprises one or more light-emitting diodes (LEDs). Alternatively, the light source 22 can be embodied by, for example and without being limitative, a solid-state lighting including lasers, organic LEDs (OLEDs), incandescent lighting, halogen lighting, fluorescent light, infrared heat emitters, discharge lighting, combinations thereof or the like. It is to be noted that the light source 22 can either emit in a continuous regime or in an intermittent regime (e.g., flashing). The light source 22 can be selected based on different properties, such as, for example and without being limitative, its spectral profile, its power and its stability. In some embodiments, the light source 22 is a sun simulator. It will be readily understood that the output beam can be coupled to optical components (not shown) configured to alter at least some of the properties of the output beam prior its interaction with the samples. The expression "optical components" herein refers, but is not limited to lenses, mirrors, filters, and other suitable reflective, refractive and/or diffractive optical components. The spectral profile of the output beam is generally large, and can range, for example and without being limitative from about 250 nm to about 2500 nm. In some embodiments, the spectral profile includes at least a UVA band (i.e., between about 315 nm to about 400 nm) and a UVB band (i.e., between about 280 nm and about 315 nm), or at least an UV component. In some embodiments, the light source 22 includes a plurality of light emitters, each being configured to generate a respective sub-beam. Each sub-beam can either be similar or different, depending on the experimental conditions.

The system 20 includes an apparatus 24 (also referred to as a spacer 24) mountable to the light source 22 for maintaining a fixed distance (sometimes referred to as a "constant distance") between the light source 22 and the skin. Such a fixed distance can help, in the case on in vivo analysis, maintaining a substantially constant dose from one experiment to another, thereby improving the reliability and reproducibility of the measurements.

The spacer 24 includes a frame 26 that includes an outer periphery 28, an inner periphery 30 and a skin-contacting portion 32. The skin-contacting portion 32 is the portion of the frame 26 that is in physical contact with the skin, and corresponds, in the illustrated embodiments, to the bottom portion 52 of the frame 26. The inner periphery 30 defines a hollow region 34 therein, i.e., a region that is empty or without material, by opposition to the solid portion of the frame 26. The hollow region 34 is such that when the skin-contacting portion 32 is engaged with the skin, the output beam can pass through the hollow region 34 and then interact with the skin being coated with the ultraviolet-protection product. The output beam interacts with the skin at an illumination plane 36 and defines an illuminated area 38 strictly confined in the hollow region 34. The illuminated area 38 can take any shape. For example and without being limitative, the shape of the illuminated area 38 can be round, square, rectangular or any other shape. In some embodiments, the illuminated area 38 does not touch the frame 26, meaning in other words that the output beam has a spot size that is smaller than the dimensions of the hollow region 34.

More particularly, the inner periphery 30 of the frame 26 is separated from an outer perimeter 40 of the illuminated area 38 by a non-null distance 41. More specifically, the distance between the outer perimeter 40 of the illuminated area 38 and the inner periphery 30 of the frame 26 is such that it can accommodate or compensate for a displacement of the sample or the participant without perturbating the quantity or the distribution of ultraviolet-protection product being exposed to the output beam in the illuminated area 38. Generally speaking, the illuminated area 38 is far enough from the inner periphery 30, such that even if some portion of the ultraviolet-protection product provided near the frame 26 or its inner periphery 30 moves away or pushes the ultraviolet-protection product, the thickness of the ultraviolet-protection product in the illuminated area 38 remains substantially constant in the illuminated area 38. As such, the spacer 24 has a double function of maintaining a fixed distance between the light source 22 and the skin, and accommodating for variations in the skin or sample position (e.g., the movements of the participant), in a manner that the region of the skin being irradiated in the illuminated area 38 has a substantially constant thickness of ultraviolet-protection product thereon during the time of the experiment while being maintained at a fixed distance from the light source 22. More particularly, the positioning of the skin-contacting portion 32 relative to the illuminated area 38 is such that upon movement of the subject causing disruption of the ultraviolet-protection product under or directly around the skin-contacting portion 32, the ultraviolet-protection product under or directly around the illuminated area 38 is substantially unaffected (i.e., substantially not altered).

The spacer 24 includes a mounting bracket 42 mechanically connected to the frame 26 and engageable with the light source 22 or with any addon or extender element that is mounted to the light source 22. The mounting bracket 42 is sized, positioned and configured for mounting the spacer 24 to the light source 22 or to an addon or extender element that is mounted to the light source 22. In this regard, the spacer 24 can be mounted to the light source 22 or to an addon or extender element that is mounted to the light source 22 using different devices, means or techniques. In one embodiment, the mounting bracket 42 is clipped on the light source 22 or to an addon or extender element that is mounted to the light source 22, for example and without being limitative, using clamps provided either on the light source 22, on an addon or extender element that is mounted to the light source 22, or on the mounting bracket 42. Alternatively, the mounting bracket 42 can be mounted to the light source 22 or to an addon or extender element that is mounted to the light source 22 using a magnet. In another embodiment, the spacer 24 is slidably mountable to the light source 22 or to an addon or extender element that is mounted to the light source 22. In this embodiment, the mounting bracket 42 has a pair of rails 44a,b mechanically engageable with a corresponding pair of guides provided on the light source 22 or on an addon or extender element that is mounted to the light source 22. Of course, the rails can be provided on the light source 22 or on an addon or extender element that is mounted to the light source 22 and, in this instance, the guides would be provided on the mounting bracket 42. It will be understood that the guides and rails are configured to mechanically cooperate and generally extend along a same direction, e.g., a horizontal axis parallel to the skin.

Figure 2B:
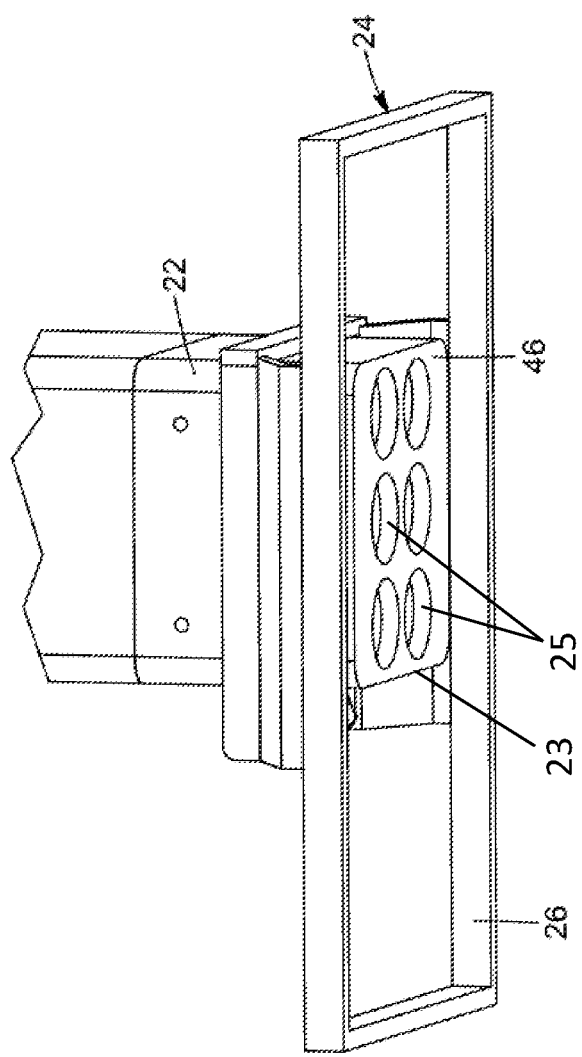
Figure 3B:
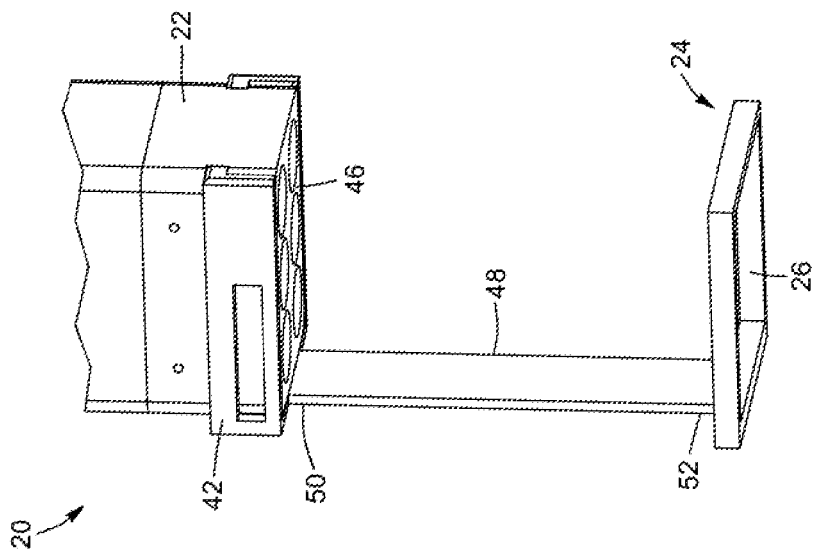
FIGS. 3A-F illustrate a system for evaluating ultraviolet-protection products, in accordance with one embodiment, and an embodiment of an apparatus for maintaining a fixed distance between a light source and a sample under investigation.
Figure 3A:
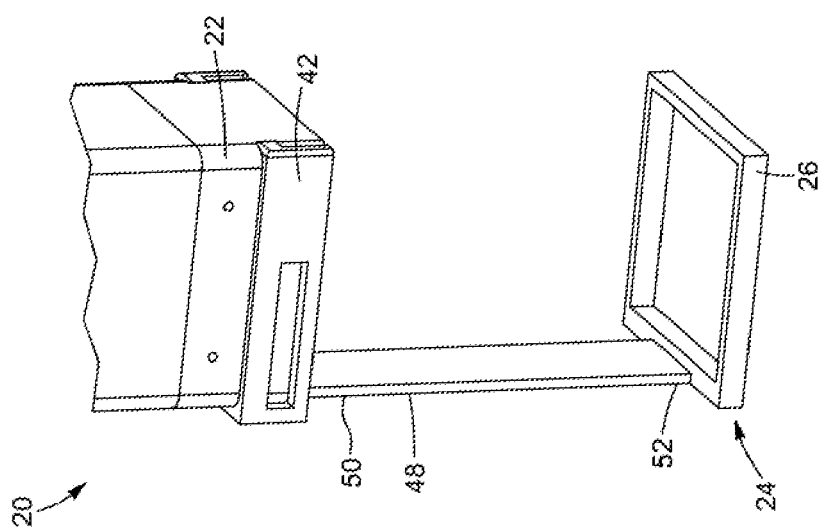
Figure 3D:
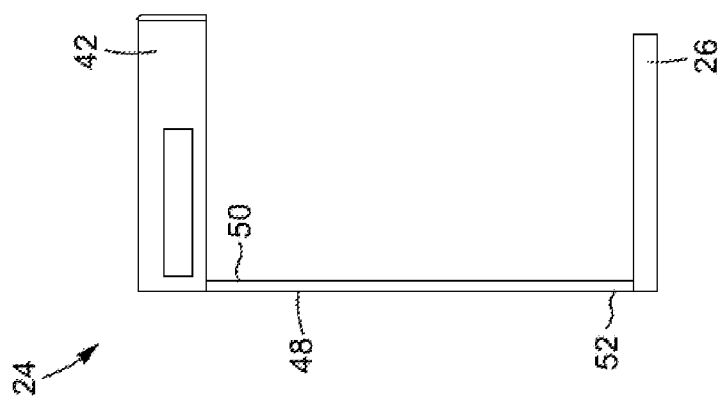
Figure 3C:
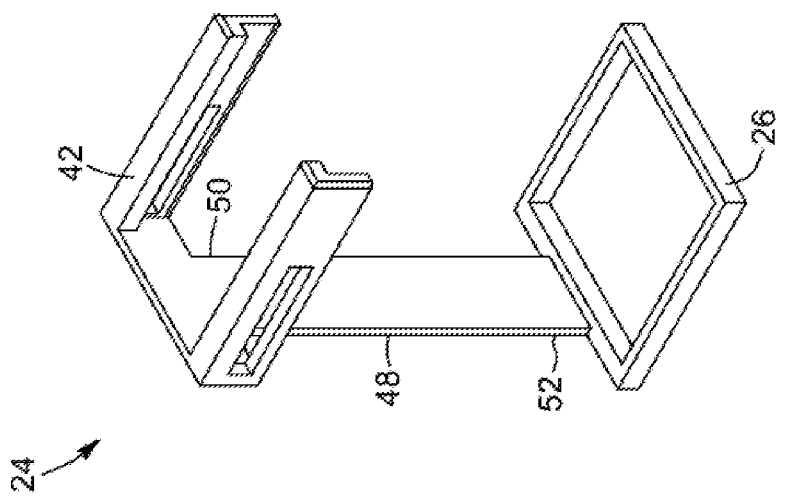
Figure 3F:
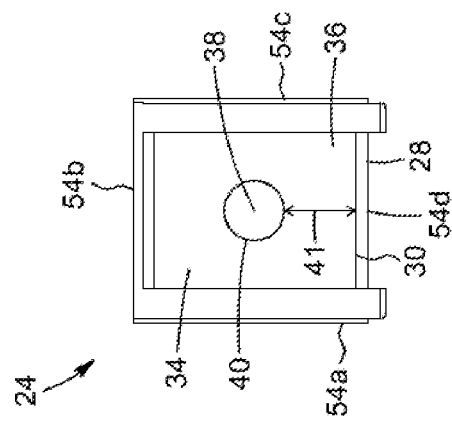
Figure 3E:
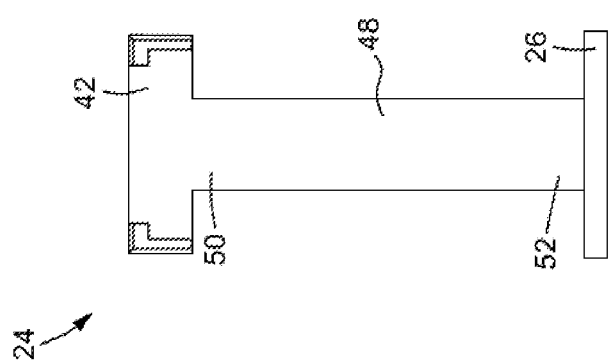

In some embodiments, for example as seen at FIGS. 1B and 2B, the light source 22 includes an addon or extender element 23. The extender element 23 includes a plurality of cavities 25, each cavity 25 surrounding a light-emitting element or light-emitting assembly of the light source (e.g., a light bulb, a LED, a LED assembly or any other light-emitting element/assembly). In the case of the embodiment of FIGS. 1B and 2B, six cavities 25 are present, each cavity surrounding a corresponding light-emitting element or light-emitting assembly (not shown on the Figures). It is understood that the spacer 24 can be attached directly to the light source 22, or to any part thereof, such as to the extender element 23, so long as the light being emitted from the light source 22 (i.e., an output beam) can freely pass through hollow region 34 and interact with the sample (e.g., skin).

As illustrated, the frame 26 is extending longitudinally outwardly from the mounting bracket 42. For example, and without being limitative, the frame 26 can have an elongated shape, meaning that the longitudinal dimension of the frame 26 can be greater than its transversal dimension. In this example, the frame 26 extends or projects away from the mounting bracket 42 along the longitudinal dimension of the frame 26, and so the frame 26 is generally longer than the mounting bracket 42. In some embodiments, the transversal dimension of the frame 26 and the mounting bracket 42 can be substantially similar, or the transversal dimension of the frame 26 can be slightly greater than the transversal dimension of the mounting bracket. The perimeter defined by inner periphery 30 of the frame 26 is generally greater than the outer perimeter of the mounting bracket 42. As it has been previously mentioned, in use, the output beam passes through the hollow region 34 and interacts with the skin at the illumination plane 36 to define the illuminated area 38 confined within the hollow region 34. This configuration allows the ultraviolet-protection product remaining substantially unaffected in the illuminated area 38 upon relative movement of the skin with respect to the frame. Such a relative movement of the skin can be imparted, for example and without being limitative, by the subject onto which the ultraviolet-protection product has been applied.

In some embodiments, the light source 22 has an illumination output portion 46 corresponding to a section of the light source 22 wherein the output beam is outputted from the light source 22. In some instances, the illumination output portion 46 is the bottom portion of the light source 22. The spacer 24, and more specifically the mounting bracket 42 can be mountable to the illumination output portion 46 of the light source 22.

In some embodiments, such as the one illustrated in FIGS. 3A-F, the spacer 24 further includes an elongated member 48 having a top portion 50 and a bottom portion 52, the top portion 50 being connected to the mounting bracket 42 and the bottom portion 52 being connected with the frame 26, the elongated member 48 longitudinally extending from the top portion 50 towards the bottom portion 52 in a vertical direction substantially perpendicular to the illumination plane 36. The elongated member 48, by its dimensions, generally allows providing a greater fixed distance between the skin or the sample and the light source 22, in comparison to the embodiments in which the elongated member 48 is not provided, as illustrated, for example and without being limitative, in FIGS. 2 and 3.

In the nonlimitative embodiments illustrated in FIGS. 1C-F and 3C-F, the frame 26 comprises four sidewalls 54a-d. In the depicted embodiments, the opposite sidewalls have the same dimensions. Of course, the dimensions of the sidewalls, as well as their number, may vary. While the frame 26 is illustrated as having a generally rectangular shape, and more particularly has a rectangular cross-section extending substantially parallel to the illumination plane 36, it would be understood that the shape of the frame 26 can vary. For example, and without being limitative, the frame 26 can be circular, and can have a single wall defining the hollow region 34. The frame 26 can be provided as a single piece or, alternatively, as a plurality of pieces assembled together. In the latter case, one or more sidewalls can be joined together using know fastening means.

As it has been previously mentioned, the skin-contacting portion 32 is generally defined by a bottom portion 52 the frame 26, which can be, depending on the configuration of the frame 26, the bottom portion 52 of the sidewall(s) forming the frame 26. In operation, the skin-contacting portion 32 is in physical and mechanical contact with the skin and abuts the same. This physical and mechanical contact allows maintaining a substantially fixed distance between the light source 22 and the skin, which can be beneficial for the reliability and repeatability of the tests. The fixed distance is generally predetermined before carrying out a series of test and maintained during the whole duration of the test, but the fixed distance can, in some embodiments, be varied from one experiment to another, for example and without being limitative, for adjusting the light dose received by the skin or the exposure of the skin. As such, the distance between the light source 22 and the skin is constant, yet adjustable, to accommodate different experimental conditions and provide the system 20 with greater flexibility.

Now turning to the materials composing the spacer 24, it has to be noted that a broad variety of materials can be used, and that the nonlimitative following examples serve an illustrative purpose only, and thus should not be considered as limiting.

The spacer 24 is generally made from a UV light resistant material to prevent the degradation of the spacer 24 over time. Alternatively, the spacer 24 can be made from a material that is not UV light resistant, but such a material can be covered by a layer or treated by an appropriate surface treatment to provide protection from the UV light and its possible degradation. In some embodiments, the spacer 24 is made from a material resistant to the wavelengths composing the spectral profile of the output beam produced by the light source 22.

The spacer 24 is typically made from a low thermal conductivity material to prevent the spacer 24 from conducting the heat generated by the light source 22 towards the skin under investigation. Similarly, the spacer 24 can be made from a material that resist relatively high temperature to prevent its degradation when exposed to the illumination beam and/or the heat generated by the light source 22. In some instances, the temperature of the light source 22 can reach about 20° C. to about 40° C., and so the spacer 24 be minimally thermally resistant to this temperature.

The spacer 24 is generally made from a biocompatible material, in order to minimize the potential negative interaction between the spacer 24 and the skin being characterized. For example, and without being limitative, the biocompatible material can be selected from polyurethane, polyamide, titanium, stainless steel, ultra high molecular weight polyethylene, medical grade silicone, poly(methyl methacrylate), acrylonitrile butadiene styrene, polyetherimide, polyether ether ketone, a polyaryletherketone (PAEK) such as polyetherketoneketone (PEKK), acrylonitrile styrene acrylate and polycarbonate. In some embodiments, the stainless steel is nickel-free. In some embodiments, the polyurethane is without additives.

Now that the materials composing the spacer 24 have been described, the geometrical configurations, the dimensions and design parameters of the spacer 24 will now be described in greater detail.

It has to be noted that there is a geometrical relationship between the size of the illuminated area 38, namely the spot size of the output beam, and the dimensions of the spacer 24 and the frame 26. Indeed, as it has been previously mentioned, the illuminated area 38, which is the result of the output beam interacting with the skin at the illumination is strictly confined within the hollow region 34. The dimensions of the hollow region 34 are dictated by the size and dimension of the frame 26, and more particularly the inner periphery 30.

Further than being strictly confined within the hollow region 34, the illuminated area 38, and more particularly its outer perimeter 40 thereof is separated from the inner periphery 30 by a non-null distance 41. The distance measured between the outer periphery 28 and an inner periphery 30 of the frame 26 defines a dimension that can correspond to a width of the wall. However, in some implementations, the wall can be much wider, and so the ratio between the non-null distance 41 and the width of the walls can differ. One would have understood that the non-null distance 41 has a minimal value that correspond to the distance required to allow or accommodate slight variations of the skin during the test, in a way that the thickness of the ultraviolet-protection product coating the skin will not be affected in the region of the illuminated area 38, which enable more reliable testing of the ultraviolet-protection product. For example, the ratio between the non-null distance 41 and the width of the walls can vary between 1:1 and 20:1, or between 1:1 and 10:1, or between 1:1 and 5:1.

Now turning to FIGS. 4A-B, an embodiment of a system 20 for evaluating an ultraviolet-protection product coating a sample is illustrated. The system 20 according to this embodiment is similar to the ones which have been previously described, as it includes a light source 22 generating an output beam having a natural light spectral profile a light source 22. In operation, the output beam interacts with the sample at an illumination plane 36 to define an illuminated area 38. The system 20 also includes a spacer 24 mountable to the light source 22 for maintaining a fixed distance between the light source 22 and the skin. The spacer 24 according to this embodiment is different than the various embodiments of the spacer 24 which have been previously described in that it the frame 26 includes a sample stage 56 for receiving the sample thereon. As such, the system 20 according to this embodiment allows supporting a sample, for example an in vitro sample on the sample stage 56, rather than illuminating the same through a hollow portion provided in the frame 26. The spacer 24 includes a mounting bracket 42 engageable with the light source 22, similarly to what has been previously described. The spacer 24 also includes an elongated member 48 having a top portion 50 and a bottom portion 52, the top portion 50 being connected to the mounting bracket 42 and the bottom portion 52 being connected with the frame 26, the elongated member 48 longitudinally extending from the top portion 50 towards the bottom portion 52 in a vertical direction substantially perpendicular to the illumination plane 36. As such, this embodiment of the system 20 is compatible with in vitro approaches rather than in vivo approaches.

It will be understood that the system 20 herein disclosed, as well as its components and associated systems are generally compliant or can be used in testing that comply with standards that are well-known in the industry. Nonlimitative examples of such standards are FDA 2011, ISO 24444, ISO 24442 and Colipa method. It has to be noted that the system 20 can be compliant or can used in testing that complies with one or more of the aforementioned standards.

Methods for Evaluating an Ultraviolet-Protection Product Coating a Skin

In accordance with another aspect, a method for evaluating an ultraviolet-protection product coating a skin will now be described. The method relies on using a light source 22.

The method includes a step of contacting the skin with a spacer 24 mounted to the light source 22 to maintain a fixed distance between the light source 22 and the skin, the spacer 24 comprising a mounting bracket 42 engageable with the light source 22 and a frame 26 comprising an outer periphery 28, an inner periphery 30 and a skin-contacting portion 32, the inner periphery 30 defining a hollow region 34 therein. The frame 26 is mechanically connected to the mounting bracket 42 and extends longitudinally outwardly from the mounting bracket 42.

The method also includes a step of generating an output beam having a natural light spectral profile with the light source 22 towards the skin, the output beam passing through the hollow region 34 and interacting with the skin at an illumination plane 36 to define an illuminated area 38 strictly confined in the hollow region 34. The ultraviolet-protection product remains substantially unaffected in the illuminated area 38 upon relative movement of the skin with respect to the frame 26.

In accordance with another embodiments, there is provided a method for evaluating an ultraviolet-protection product coating a sample using a light source 22, the method comprising a first step of providing a spacer 24 mounted to the light source 22 to maintain a fixed distance between the light source 22 and the sample, the spacer 24 comprising a mounting bracket 42 engageable with the light source 22, a frame 26 comprising a sample stage 56 for receiving the sample thereon, and an elongated member 48 having a top portion 50 and a bottom portion 52, the top portion 50 being connected to the mounting bracket 42 and the bottom portion 52 being connected with the frame 26, the elongated member 48 longitudinally extending from the top portion 50 towards the bottom portion 52 in a vertical direction substantially perpendicular to the illumination plane 36. The method also includes mounting the sample on the sample stage. The method also includes generating an output beam having a natural light spectral profile with the light source 22 towards the sample.

It will be understood that the methods herein disclosed is generally compliant or is compatible with testing that comply with standards that are well-known in the industry. Nonlimitative examples of such standards are FDA 2011, ISO 24444, ISO 24442 and Colipa method. It has to be noted that the method can be compliant or can used in testing that complies with one or more of the aforementioned standards.

EXAMPLES

Example 1: In Vivo Evaluation of the Sun Protection Factor (SPF) of a Sunscreen Product According to ISO 24444:2010 International Standard 1. Introduction 1.1. Characteristics of the Panel The study was performed on male and female volunteers, with age between 18 and 70 years, who were identified from a database of volunteers.

Before the beginning of the study, each volunteer read and signed an informative form and answered its questions exhaustively. Each volunteer had the opportunity to ask questions regarding the study to which an exhaustive answer was given. The objectives of the test, the procedures and the possible related risks were explained to the volunteers.

The participation in the study was permitted only after signature of the informed consent. Only volunteers in good general health conditions were included in the study. All volunteers signed a consent form allowing to treat personal data according to the Québec Law.

The subjects included in the SPF test panel were of phototype I, II, or III according to the Fitzpatrick scale, or had have an ITA° value>28°, determined by colorimetric methods and were untanned on the test area. The correlation between the cutaneous phototype, the color of the skin and the ITA° value is represented in the following table:

| Phototype | Description | ITA° values |
|---|---|---|
| I | VERY LIGHT | >55° |
| II | LIGHT | >41 to 55° |
| III | INTERMEDIATE | >28 to 41° |
| IV | TAN (or MATT) | >10 to 28° |
| V | BROWN | >−30 to 10° |
| VI | BLACK | ≤−30° | where ITA° = [arctg((L* − 50)/b*)] × 180/3.1416

Moreover, the following criteria of exclusion were applied:

Pregnancy or nursing condition (except where explicitly required);

Blemishes, marks, including tattoos, scars, sunburns on the test site(s) which could interfere with scoring;

Medication (local and/or systemic) which may affect skin response;

Signs of irritated skin on test site(s);

Any active skin disease which may interfere with the aim(s) of the present study;

Absence of skin hyperpigmentation problems caused by exposure to solar radiation;

Participation in other simultaneous studies that might interfere with the test evaluation or participation in a previous study without an appropriate rest period between studies.

After the study started, the following withdrawal criteria were applied:

Volunteers who did not follow the conditions as described in the Study Information Sheet;

Volunteers who suffered any illness or accident or developed any condition which could affect the outcome of the study;

Volunteers who not longer wished to participate in the study.

There was a sufficient interval between two successive UV exposures to the same test site for resolution of discoloration resulting from previous tests.

1.2. Aim of the Test

The aim of the test was to determine in vivo the static Sun Protection Factor (SPF) of a sunscreen product according to ISO International Standards. The SPF testing procedure was carried out according to the ISO 24444:2010 International Standard, "Sun protection test methods—In vivo determination of the sun protection factor (SPF)".

2. Preparation of the Test Sample

The sunscreen product did not undergo any preliminary treatment.

Liquid type products consisting of two layers were shaken strongly before weighing in order to ensure a homogeneous dispersion. In the case of powder products, aliquots of powder should be transferred to the skin in a grid-like manner, using a spatula or finger. Purified water or another suitable solvent that has no UV protection properties may be applied before the powder application to help the sample adhere to the application site.

Before product application, the test area may be cleaned, but only by using a dry cotton pad or equivalent.

3. Amount of Substance Applied

The product was spread out uniformly on the skin of the volunteers such as to obtain a quantity of test substance on the test site of 2.0±0.05 mg/cm2. A visual control of the product, as well as a gravimetrical control with an analytical balance (0.1 mg resolution), were made before the measure.

4. Method of Application

A double weighing procedure was incorporated as follows: positive pipette with pipette tip/syringe/spatula+product+finger cot, prior to and after application to ensure the required quantity was delivered.

To assure an uniform distribution, little droplets of the product are deposited with a positive pipette/syringe/spatula, then spread with a finger cot over the whole test site with light pressure using circular and then linear movements (up and down). Spreading time was in the range of 20 to 50 seconds. Product is applied as evenly as possible.

Homogeneity of the application is verified by using a Woods lamp.

The sample is applied to the back of the volunteers in such a way to obtain a constant thickness so that the length of the UVA rays' pathway through the sample can be considered homogeneous in each point.

5. Site of Exposure

The site of exposure was an area of 50 $cm^2$ in the inter-scapular region of the back. The sites did not present skin damages nor naevi nor hair or any other anomaly which could prevent regular testing and is not tanned. Skeletal protrusions and extreme areas of curvature were avoided.

The ITA value of each testing site was obtained by the Chromameter. Three measurements on each sub site. The ITA value was then used to determine the skin phototype and MEDu Each test site encompassed six round shaped sub-sites of about 1 cm² each in size, corresponding to the optical guides of the Solar UV Simulator. The minimum distance between the borders of each exposure sub-site was 0.8 cm. A dermal graphic pen, not water soluble was used to demarcate the sites of exposure.

According to the Experimental Plan, test sites were randomised in order to reduce standard error due to skin tone differences.

The unprotected test site used to determine the MEDu was in close proximity to the MEDp test sites.

6. Waiting Time Between Application and Uv Exposure

Exposure of the test site to the sequence of UV doses started about 15-30 minutes after application of the product.

7. Equipment

UV Source: the UV irradiation was performed with a UV Solar Simulator Model 601-300 V2.5 from SolarLight Co., equipped with a Xenon Arc Lamp 300 W, in compliance with FDA-COLIPA standards. The device was equipped with Shutter (UVA-B) WG320 and UG 11 black glass filters and with a LLG of the appropriate size.

The table below reports the spectral emission in % RCEE (Relative Cumulative Erythema) Effectiveness) with acceptability limits:

| Spectral range (nm) | % RCEE lower limit | % RCEE upper limit |
|---|---|---|
| <290 | n/a | <0.1% |
| 290-300 | 1.0 | 8.0 |
| 290-310 | 49.0 | 65.0 |
| 290-320 | 85.0 | 90.0 |
| 290-330 | 91.5 | 95.5 |
| 290-340 | 94.0 | 97.0 |
| 290-400 | 99.9 | 100.0 |

The output signal of the Solar Simulator was evaluated with the aid of a certified Dose Control System (DCS-2.0) with a LLG adaptor and with two detectors (Erythema detector PMA2108 LLG and UVA detector PMA 2118 LLG).

Chromameter: The skin phototype of the volunteers was measured with a Konica-Minolta CR-400. Colorimetric readings were expressed in ITA values.

Analytical balance: Balance: 1; Code: INS-012; Model: Cole Parmer SYMMETRY PA 120 (120 g±0.0001 g).

Doctor bed to position the volunteers.

Gilson positive pipette, syringe or spatula (for solid products) used to weight and apply the products.

Dermographic pen to delineate the skin area of application of the products and the area of contact with the six probes.

Plexiglass support (dimensions 5 cm×10 cm) to define the area of application of the product.

Finger cot for the product application.

Environmental Thermometer to verify the room temperature during the test.

8. UV Exposures

A warm up of about 10 minutes was allowed for the UV Solar Simulator to stabilize before starting the exposure of the subjects. Subjects were exposed in prone position to the appropriate amount of UV radiation.

The irradiation time change according to the MED calculated for each subject (the MED for unprotected skin of phototype I, II and III)

Before the UV exposure of each test site, the output UV irradiance of each of the six guides of the Solar Multi port was verified with the detector.

9. Minimal Erythemal Dose (MED)

The minimal erythema dose (MED) is defined as the lowest ultraviolet UV dose that produces the first perceptible unambiguous erythema with defined borders appearing over most of the field of UV exposure, 16 to 24 hours after UV exposure.

10. Incremental Progression of UV Dose

Six sub-sites centered on the expected MED were exposed to incremental UV doses using a geometric progression of 1.12 to 1.25.

For all the exposures (MED and test product), the six different doses were administered following a geometric progression of 1.15.

11. Product Removal

After US exposures, standard and tests products were removed gently from the skin of the volunteers using a cotton pad.

12. Med Assessment Procedure

The minimal erythema dose for unprotected skin (MEDu), that for protected skin (MEDp) and that for the standard sunscreen product are determined on the same day.

The MED was assessed 20±4 hours after UV exposure. The MED was assessed visually by a trained specialist. Visual assessment was performed in sufficient and uniform illumination (>500 lux).

The MED for each site was identified as the lowest dose to generate a perceptible, unambiguous erythema covering most of the field of the UV exposure and with clearly defined borders.

MED are expressed in terms of energy/surface (mJ/cm²).

13. Sun Protection Factor

An individual Sun Protection Factor (SPFi) value for a product is defined as the ratio of the MED of product protected skin–tpMEDp (mJ/cm²) and the MED of unprotected skin–MEDu (mJ/cm²) for the same subject.

$$SPFi=tpMEDp/MEDu$$

The SPF for the product is the arithmetic mean of all valid SPFi obtained from all the subjects in the test, expressed to one decimal place.

14. Data Rejection Criteria

Test data shall be rejected under the following circumstances:

The exposure series on a subject failed to elicit an erythemal response on a test site 20±4 hours after exposure;

Erythemal responses within an exposure series were randomly absent 20±4 hours after exposure;

All sub-sites in the exposure series showed an erythemal response 20±4 hours after exposure.

15. Experimental Design

Day 1:

Conducted ITA Measurement

Each test site should be outlined with Dermographic pen. Test subsites are the locations to which UV radiation is administered within a test site. Test subsites should be separated from each other by at least 0.8 cm Apply the sunscreen test product at 2.0±0.05 mg/cm² to their respective test sites. If used, choose finger cot compatible with the sunscreen to spread the product and standard homogenously over randomly chosen test sites on the back of the volunteers.

Wait at least 15 minutes after applying a sunscreen product or standard before exposing the test sites to UV radiation.

block surrounding the optical guides of the Solar UV Simulator for the measurements "with spacer". For the values measured "without spacer", the light source was positioned as close as possible to the back of the volunteer, typically at about 1 to 2 cm. The results are summarized in the Tables below:

TABLE 1

SPF measurements with and without spacer

| Volunteer # | GENDER | AGE | Standard Value | Value measured with spacer | % Variation with spacer | Value measured without spacer | % Variation without spacer |
|---|---|---|---|---|---|---|---|
| 1 | F | 18 | 16.50 | 17.00 | 3.03% | 14.78 | −10.41% |
| 2 | M | 37 | 16.50 | 16.50 | 0.00% | 12.48 | −24.35% |
| 3 | F | 47 | 16.50 | 14.06 | −14.76% | 12.54 | −24.00% |
| 4 | F | 18 | 16.50 | 18.97 | 14.94% | 16.50 | 0.00% |
| 5 | M | 38 | 16.50 | 16.50 | 0.00% | 14.41 | −12.64% |
| 6 | M | 37 | 16.50 | 16.50 | 0.00% | 16.50 | 0.00% |
| 7 | F | 62 | 16.50 | 14.36 | −13.00% | 10.88 | −34.09% |
| 8 | F | 22 | 16.50 | 18.94 | 14.78% | 18.94 | 14.78% |
| 9 | F | 53 | 16.50 | 12.48 | −24.35% | 12.50 | −24.24% |
| 10 | F | 51 | 16.50 | 18.94 | 14.78% | 16.50 | 0.00% |
| 11 | F | 38 | 16.50 | 16.50 | 0.00% | 18.94 | 14.78% |
| 12 | F | 37 | 16.50 | 16.50 | 0.00% | 16.50 | 0.00% |
| 13 | F | 57 | 16.50 | 14.41 | −12.64% | 12.54 | −24.00% |
| 14 | F | 43 | 16.50 | 14.35 | −13.04% | 10.90 | −33.91% |
| 15 | M | 25 | 16.50 | 21.81 | 32.18% | 16.50 | 0.00% |
| 16 | F | 35 | 16.50 | 16.50 | 0.00% | 16.50 | 0.00% |
| 17 | F | 29 | 16.50 | 12.48 | −24.35% | 12.48 | −24.35% |
| 18 | F | 46 | 16.50 | 18.97 | 14.94% | 17.28 | 4.74% |
| 19 | F | 45 | 16.50 | 14.36 | −13.00% | 16.50 | 0.00% |
| 20 | F | 47 | 16.50 | 18.89 | 14.47% | 14.33 | −13.16% |
| AVERAGE | | 39.25 | 16.50 | 16.45 | −0.30% | 14.93 | −9.54% |
| Standard Deviation | | | | 2.455 | — | 2.487 | — |
| P Value | | | | — | 0.9290 | — | 0.0107 |

For each test subject, administer a series of UV radiation doses expressed as $mJ/cm^2$ to the test subsites within an unprotected test site using an accurately calibrated solar simulator. Select doses that are a geometric series represented by 1.12 to 1.25n.

UV exposure for final unprotected MEDu ($mJ/cm^2$) and testing product tpMEDp ($mJ/cm^2$) at the appropriate test sites.

Day 2:

Evaluation of erythema on test subsites.

Determine the MED 16 to 24 hours after UV exposure. The person who evaluates the test should not be the same person who applied the sunscreen product to the test site or administered the UV doses. After UV doses are administered, all immediate responses should be recorded.

The final unprotected MEDu ($mJ/cm^2$ and testing product tpMEDp ($mJ/cm^2$) are determined.

16. Results Expression and Interpretation

The product's UV protection is measured in the UV range between 290 nm and 400 nm.

The SPF result for the test product is calculated as the arithmetical mean of all valid individual SPFi values.

17. Results

Tests were conducted on 20 volunteers, following the above-described testing protocol, using a UV-protection product standard having an SPF value of 16.50. For each volunteer, tests were conducted with and without the apparatus (spacer) of FIGS. 1A-F attached to the light source. More specifically, the spacer was attached to a monolithic

TABLE 2

MEDu measurements with and without spacer
MEDu

| Probe | With spacer | Without spacer |
|---|---|---|
| Probe 2 | 0 | 15% |
| Probe 3 | 30% | 15% |
| Probe 4 | 35% | 10% |
| Probe 5 | 35% | 35% |
| Probe 6 | 0 | 25% |

Example 2: Material for the Spacer

The purpose of the test is to assess the absence of pro-sensitizing skin effects from finished products or raw materials intended for contact with the skin or mucous membranes, such as medical devices, cosmetics, toys or textiles. In the present study, we used a human monocytes cell line (THP-1) as prototypic blood-derived immunologically active cell. On these cells, we tested the expression of two costimulatory molecules, CD54 (Intercellular Adhesion Molecule) and CD86 (B7.2), using as a positive control Nickel sulphate, a well-known contact sensitizing agent. Nickel sulphate is able to cause in vivo allergic immune reactions (skin sensitization) and it is also been widely used to study in vitro immune response modulation. As silicone elastomer (Silicone 30A—example of medical grade silicone) was tested at two concentrations, against Nickel positive controls.

The increasing expression level of CD54 and CD86 on monocytes is a signal of activation of the immune response derived from the exposition to a potentially sensitizing contact antigen. The expression of co-stimulatory molecules on the dendritic cells means activation of the immunological response in terms of capability to present the antigen in the typical tissues (skin in this case), where, in vivo, the immune protective response is triggered.

The normative reference is OECD Guideline 442E, "In vitro Skin Sensitization; Human Cell Line Activation Test (hCLAT)", which is hereby incorporated by reference in its entirety. The method differs from the OECD Guideline as the test is performed in a single experimental session instead of three independent tests. As positive control, Nickel Sulfate is used instead of DNCB. A preliminary cytotoxicity is also performed to select the two highest concentrations that do not cause cytotoxic effects. In addition, the acceptance criteria and choice of concentrations to be used in the final test have been optimized according to the laboratory's historical results over the past 10 years.

The test is carried out on a monocyte-like human line called THP-1. Cells are kept in RPMI containing 10% FCS and 2 mM glutamine.

The sample has been eluted in phosphate buffered saline (1 g/5 ml) for 24 hours at 37° C. The eluted sample was diluted in the cell culture medium at different concentrations for the preliminary cytotoxicity screening on the cells aimed to decide the best concentration to test it without cytotoxic effects on the monocytes, in order to avoid false results. Cell medium exposed to the same experimental conditions were used as a negative control.

Following the results of the preliminary assay, the eluted sample was diluted directly in the cell medium at the two different dilutions in order to obtain the desired final concentrations in contact with the THP-1 cells in vitro. The exposure has been carried out for 24 h at 37° C. with 5% $CO_2$.

After the incubation with the tested substance and the controls, cells are collected, checked under the microscope for their viability by staining with Trypan Blue dye and counting in a cell counter chamber, washed in PBS and then marked with a fluoresceinated anti-Intercellular Adhesion Molecule (CD54) or B7.2 (CD86) antibody and in both cases with a propidium iodide (PI) solution to simultaneously measure the percentage of dead cells. To this aim, a PI working solution (1 ml PI stock solution (1 mg PI/ml water) in 20 ml PI buffer (1 g glucose/l PBS without Ca/Mg)) is added to 105 cells. A gate is set on the negative cells in order to exclude the dead cells. Only viable cells are included for analyses of CD54 or CD86 expression. After washing, to eliminate the excess antibody, the MFI (Mean Fluorescence Intensity) linked to the cells is evaluated by means of a flux cytofluorimeter (FACS, Fluorescence Activated Cell Sorter, Becton Dickinson, Mountain View, Calif.). This value is proportional to the expression of co-stimulatory molecules.

The results are expressed in terms of MFI (Mean Fluorescence Intensity). MFI is the geometric mean of the fluorescence intensity of the cells decorated with the fluoresceinated antibody and it is proportional to the number of stained molecules per cell.

Cell vitality: The percent of living cells (PI negative) must be above 80% in all samples.

For positive control: The MFI of the positive control must be >10% of the negative control at the lowest tested concentration of nickel. The MFI must display a dose-response increasing pattern with the other two tested doses.

The costimulatory molecules expression is compared to the behaviour of Nickel, a prototypic sensitising substance, characterised by a) high increase of both the markers; b) direct correlation between concentration and intensity of the response; c) relevant effects even at very low doses. The tested dose of 4 μg/ml of Nickel Sulphate ($NiSO_4.6H_2O$) corresponds to more or less 1 ppm of Nickel, dosage that is around the minimal sensitising threshold in already sensitised individuals with irritated skin. The concentration that is able to cause an allergic reaction in most of the sensitive subjects is anyway around higher value, over the 100 ppm of Nickel Sulphate.$6H_2O$ in contact with safe and intact skin.

The MFI values are considered significantly increased as a result of incubation with the test product, when they are higher than the value of "MFI cut-off" that is obtained by increasing the MFI of the negative control by defined percentage value. The latter is obtained by dividing the mean+2 standard deviations of a series of 10 determinations of MFI performed on as 10 negative control samples for the value of the MFI of the negative control itself. This determination is carried out every six months as a measure of intra-assay variability. The results are summarized in the Table below.

TABLE 3

Evaluation of silicone 30A as a possible spacer material

| | CD54 | | CD86 | | |
|---|---|---|---|---|---|
| Sample | MFI | % compared to Negative Control (CN) | MFI | % compared to CN | PI |
| Nickel Sulfate 20 μg/ml | 65.43 | 163.94 | 102.65 | 399.03 | 86 |
| Nickel Sulfate 10 μg/ml | 40.56 | 63.61 | 50.65 | 146.23 | 86 |
| Nickel Sulfate 4 μg/ml | 33.65 | 35.74 | 26.32 | 27.95 | 88 |
| Eluate Silicone 30A Elastomer 100 μl/ml | 24.37 | −1.69 | 20.33 | −1.17 | 88 |
| Eluate Silicone 30A Elastomer 20 μl/ml | 24.43 | −1.45 | 20.43 | −0.68 | 88 |
| Negative control | | 24.71 | | 20.57 | 88 |
| MFI CUT OFF | | 25.48 | | 21.09 | — |

The results show that Silicone 30A does not affect in this in vitro model the expression of the investigated markers in immunocompetent cells, and hence it does not show any stimulating potential on the immune cellular response mediated by monocytes/macrophages.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments can be provided in any combination with the other embodiments disclosed herein. The present examples and embodiments, therefore, are to be considered in all respects as illustrative and not restrictive. Accordingly, while specific embodiments have been illustrated and described, numerous modifications come to mind without significantly departing from the scope defined in the appended claims.

The invention claimed is:

1. A system for evaluating an ultraviolet-protection product to be applied to skin, comprising:
   a light source generating an output beam having a natural light spectral profile; and
   a spacer mountable to the light source for maintaining a fixed distance between the light source and the skin, the spacer comprising:

a mounting bracket engageable with the light source, wherein the mounting bracket has a pair of rails mechanically engageable with a corresponding pair of guides provided on the light source; and a frame mechanically connected to the mounting bracket and extending longitudinally outwardly from the mounting bracket, the frame comprising an outer periphery, an inner periphery and a skin-contacting portion, the inner periphery defining a hollow region therein, such that when the skin-contacting portion is engaged with the skin, the output beam passes through the hollow region and interacts with the skin at an illumination plane to define an illuminated area confined within the hollow region.

2. The system of claim 1, wherein the light source is a sun simulator.

3. The system of claim 1, wherein the natural light spectral profile ranges from about 250 nm to about 2500 nm.

4. The system of claim 1, wherein the natural light spectral profile comprises a UVA band and a UVB band.

5. The system of claim 1, wherein the light source comprises a plurality of light emitters, each being configured to generate a respective sub-beam.

6. The system of claim 1, wherein the mounting bracket is clipped on the light source.

7. The system of claim 1, wherein the mounting bracket is slidably engageable with the light source.

8. The system of claim 1, wherein the light source has an illumination output portion, the spacer being mountable to the illumination output portion of the light source.

9. The system of claim 1, wherein the frame comprises four sidewalls.

10. The system of claim 1, wherein the frame has a rectangular cross-section extending substantially parallel to the illumination plane.

11. The system of claim 1, wherein the spacer is made from a UV light resistant material.

12. The system of claim 1, wherein the spacer is made from a low thermal conductivity material.

13. The system of claim 1, wherein the spacer is made from a high-temperature resistant material.

14. The system of claim 1, wherein the spacer is made from a biocompatible material.

15. The system of claim 14, wherein the biocompatible material is selected from the group consisting of polyurethane, polyamide, titanium, stainless steel, ultra high molecular weight polyethylene, medical grade silicone, poly (methyl methacrylate), acrylonitrile butadiene styrene, polyetherimide, polyether ether ketone, polyetherketoneketone, acrylonitrile styrene acrylate and polycarbonate.

16. A spacer mountable to a light source that is part of a system for evaluating an ultraviolet-protection product to be applied to skin, the light source being configured to generate an output beam having a natural light spectral profile, the spacer comprising:

a mounting bracket engageable with the light source, wherein the mounting bracket has a pair of rails mechanically engageable with a corresponding pair of guides provided on the light source; and a frame mechanically connected to the mounting bracket and extending longitudinally outwardly from the mounting bracket, the frame comprising an outer periphery, an inner periphery and a skin-contacting portion, the inner periphery defining a hollow region therein, such that when the skin-contacting portion is engaged with the skin, the output beam passes through the hollow region and interacts with the skin at an illumination plane to define an illuminated area confined within the hollow region.

17. A method for evaluating, using a light source, an ultraviolet-protection product to be applied to skin, the method comprising:

contacting the skin with a spacer mounted to the light source to maintain a fixed distance between the light source and the skin, the spacer comprising a mounting bracket engageable with the light source, wherein the mounting bracket has a pair of rails mechanically engageable with a corresponding pair of guides provided on the light source; and a frame mechanically connected to the mounting bracket and extending longitudinally outwardly from the mounting bracket, the frame comprising an outer periphery, an inner periphery and a skin-contacting portion, the inner periphery defining a hollow region therein; and generating an output beam having a natural light spectral profile with the light source towards the skin, the output beam passing through the hollow region and interacting with the skin at an illumination plane to define an illuminated area confined within the hollow region.

* * * * *